United States Patent [19]
Kimura

[11] Patent Number: 5,635,135
[45] Date of Patent: Jun. 3, 1997

[54] TEST ELEMENT AND TEST ELEMENT CARTRIDGE

[75] Inventor: Muneyasu Kimura, Kanagawa-ken, Japan

[73] Assignee: Fuji Photo Film Co., Ltd., Kanagawa, Japan

[21] Appl. No.: 528,704

[22] Filed: Sep. 15, 1995

[30] Foreign Application Priority Data

Sep. 16, 1994 [JP] Japan ................... 6-221912

[51] Int. Cl.$^6$ ................................. G01N 21/01
[52] U.S. Cl. .................. 422/57; 436/43; 436/44
[58] Field of Search .............. 422/56–58; 436/43–44

[56] References Cited

U.S. PATENT DOCUMENTS

| | | | |
|---|---|---|---|
| 3,992,158 | 11/1976 | Przybylowicz et al. | 23/253 TP |
| 4,292,272 | 9/1981 | Kitajima et al. | 422/57 |
| 4,954,319 | 9/1990 | Koizumi et al. | 436/44 |
| 5,094,816 | 3/1992 | Ishizaka et al. | 436/44 |
| 5,096,828 | 3/1992 | Ishizaka et al. | 436/44 |

FOREIGN PATENT DOCUMENTS 53-21677  7/1978  Japan.
55-164356 12/1980  Japan.

*Primary Examiner*—Lyle A. Alexander
*Attorney, Agent, or Firm*—Sughrue, Mion, Zinn, Macpeak & Seas

[57] ABSTRACT

In a biochemical analysis apparatus, a chemical analysis element is taken out from a chemical analysis element cartridge, spotted with sample liquid and transferred to an incubator. After incubation, the optical density of the chemical analysis element is measured, and the concentration of a component to be analyzed in the sample liquid is determined. A test element which is substantially equal to the chemical analysis element in size and shape and has a density pattern for detecting shift of the position of the test element from a predetermined position is taken out from a cartridge and is transferred to the incubator in the same manner as the chemical analysis element. On the way to the incubator, the position of the test element relative to, for instance, a suction member for transferring the chemical analysis element is detected by use of the density pattern, and when it is detected that the test element is in the regular position relative to the suction member, it can be expected that the chemical analysis element can be transferred in the regular position on the suction member.

6 Claims, 7 Drawing Sheets

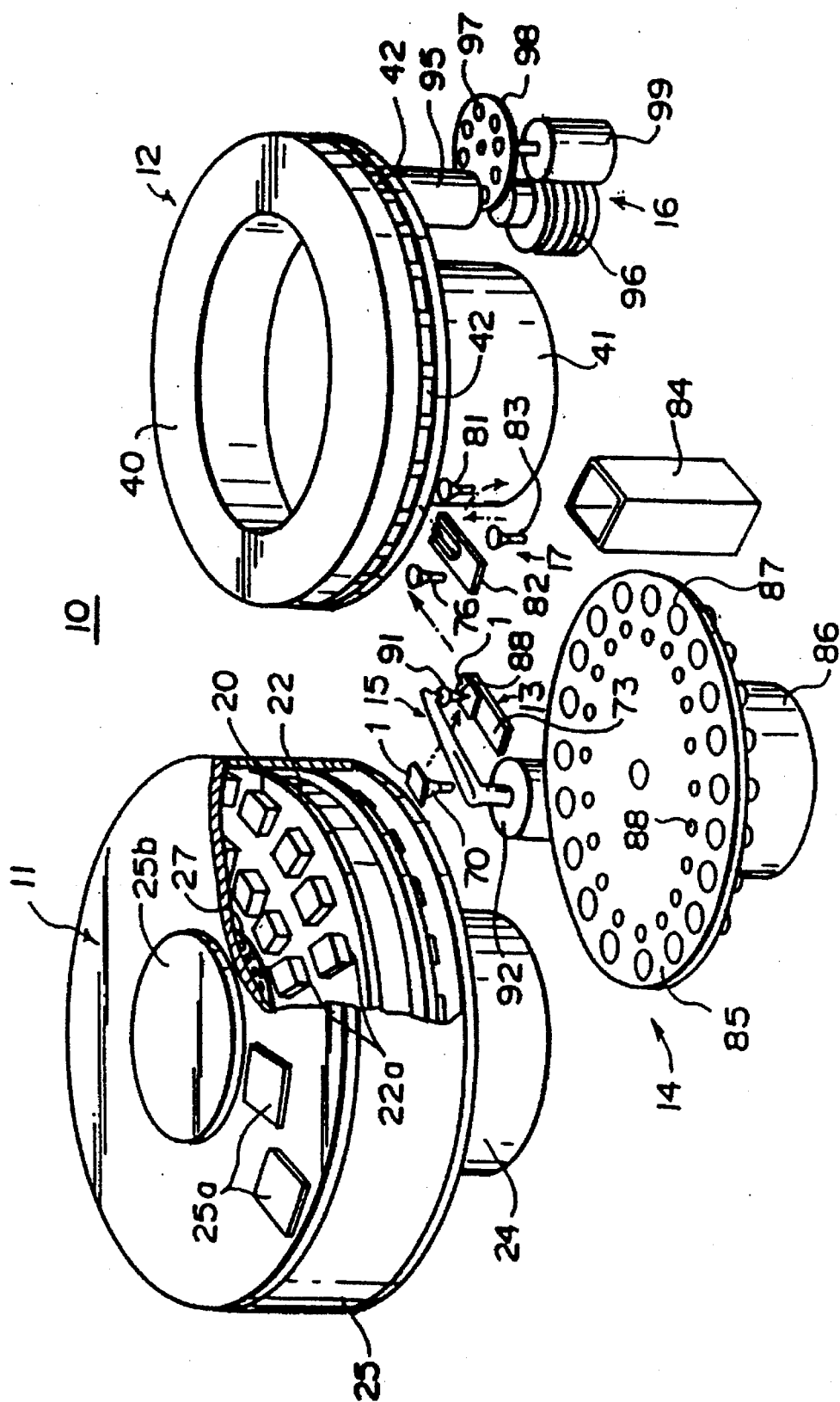

TEST ELEMENT AND TEST ELEMENT CARTRIDGE

BACKGROUND OF THE INVENTION

1. Field of the Invention

This invention relates to a test element for use in a biochemical analysis apparatus and a test element cartridge containing therein such test elements, and more particularly to a test element for detecting a shift in position of a "dry-to-the-touch" chemical analysis element in the course of transfer thereof in a biochemical analysis apparatus and a test element cartridge containing therein such test elements, the "dry-to-the-touch" chemical analysis element being an element having a reagent layer whose optical density changes upon chemical reaction, immunoreaction or the like with a specific biochemical component contained in a sample liquid such as blood or urine.

2. Description of the Related Art

Quantitative or qualitative analysis of a specific component in a sample liquid is a common operation carried out in various industrial fields. Especially, quantitative analysis of a chemical component or a solid component in body fluids such as blood or urine is very important in the field of clinical biochemistry.

There has been put into practice a dry chemical analysis film with which a specific chemical component or solid component contained in a sample liquid can be quantitatively analyzed through a droplet of the sample liquid spotted on the film. See, for instance, Japanese Patent Publication No. 53(1978)-21677, U.S. Pat. No. 3,992,158, Japanese Unexamined Patent Publication 55(1980)-164356 and U.S. Pat. No. 4,292,272. When such a dry chemical analysis film is used, the sample liquid can be analyzed more easily and more quickly than when a conventional wet analysis method is used, and accordingly the dry chemical analysis film is very convenient for medical facilities, laboratories and the like where lots of sample liquids have to be analyzed.

When quantitatively analyzing the chemical components or the like contained in a sample liquid using such a chemical analysis film, there is used a biochemical analysis apparatus in which the chemical analysis film is taken out from a cartridge and transferred to a predetermined position, a droplet of the sample liquid is spotted on the film, the film spotted with the sample liquid is transferred into an incubator and held therein at a constant temperature for a predetermined time (incubation) so that coloring reaction (coloring substance generating reaction) occurs, and the optical density of the color formed by the coloring reaction is optically measured. That is, measuring light containing a wavelength which is preselected according to the combination of the component to be analyzed (sometimes will be referred to as "analyte", hereinbelow) and the reagent contained in the reagent layer of the film is projected onto the film and the optical density of the film is measured. Then the concentration or the activity of the analyte is determined on the basis of the optical density using a calibration curve or a standard curve which represents the relation between the concentration (content) of the analyte and the optical density. After the measurement, the film is taken out from the incubator and discarded in a discarding box.

In such a biochemical analysis apparatus, the successive processings are effected while transferring the analysis film from position to position. When the analysis film is shifted from a predetermined position on a film take-out means or a film transfer means while it is taken out from the cartridge or transferred, spotting the sample liquid on the analysis film, the incubation, the measurement of the optical density and the like cannot be centered on a predetermined position on the analysis film, e.g., the central portion of the analysis film, which results in a fine difference in the measured value and substantially affects the result of determination. Accordingly, in a biochemical analysis apparatus where the accuracy of measurement is very important, there has been a demand for means for checking whether the analysis film can be held in a predetermined position on the film take-out means or the film transfer means while it is taken out from the cartridge or transferred.

SUMMARY OF THE INVENTION

In view of the foregoing observations and description, the primary object of the present invention is to provide a test element for checking whether the chemical analysis element can be held in a predetermined position on the film take-out means or the film transfer means.

Another object of the present invention is to provide a test element cartridge containing therein such a test element.

The chemical analysis film generally comprises a support sheet of organic polymer and at least one reagent layer formed on the support sheet. Preferably a spreading layer is formed over the reagent layer. The chemical analysis film is generally in the form of a film chip of a predetermined shape such as square or rectangle. The film chip is sometimes provided with a frame of organic polymer or the like for facilitating automated handling of the film chip and sometimes used as it is without a frame. The chemical analysis film with a frame is generally referred to as "a chemical analysis slide" and that without the frame is generally referred to as "a frameless chemical analysis film", Further, there have been known single-layered and multi-layered chemical analysis films formed of filter paper (with or without a frame). In this specification, the term "chemical analysis element" should be broadly interpreted to include the frameless chemical analysis film, the chemical analysis slide and the single-layered or multi-layered chemical analysis film formed of filter paper (with or without frame) as well as other like elements and devices for various analyses.

Use of the chemical analysis element in the form of slides results in increase in the size of various parts handling the elements such as cells in the incubator for incubating the elements, the transfer system, an element supplier for storing the films in dry state and the like. Thus the frame is obstructive to reducing the size of the biochemical analysis apparatus and at the same time reduces the element accommodating capacity of the incubator, which obstructs increase in the overall throughput capacity of the biochemical analysis apparatus. Further, the cost for mounting the frame is high, which adds to the cost of biochemical analysis.

Thus use of the frameless chemical analysis film is advantageous over use of the chemical analysis slides. However, the frameless chemical analysis film is more difficult to handle by an automated system than the chemical analysis slide. Accordingly we have developed a technique of carrying out the biochemical analysis using the frameless chemical analysis films. For example, there is proposed in our U.S. patent application Ser. No. 08/269,033 a biochemical analysis apparatus comprising a cartridge in which a plurality of frameless chemical analysis films are contained, a suction take-out means such as of a suction cup for taking out the frameless chemical analysis films from the cartridge without damaging the films, a suction transfer means such as of a suction cup similar to that of the take-out means for transferring the frameless chemical analysis film to a spotting position and an incubating position, a spotting means for spotting a predetermined amount of sample liquid on the frameless chemical analysis film and an incubator for incubating the frameless chemical analysis film spotted with sample liquid.

However the biochemical analysis apparatus has the following difficulties due to the fact that the frameless chemical analysis film has no frame. That is, the frameless chemical analysis film cannot be positioned by directly applying a force to the frameless chemical analysis film. Thus, the frameless chemical analysis film is taken out from the cartridge and transferred by a suction cup which attracts the film on one side thereof under suction force and the film is held in place in the incubator by pressing the corner portions of the film under a weak force. Further, since the entire area of the frameless chemical analysis film is a color developing surface (measuring surface) and at the same time the frameless chemical analysis film is small in size, it is difficult for the operator to correct the position of the analysis film on the film take-out means or the film transfer means and it is difficult to reuse the frameless chemical analysis film.

Thus, when the chemical analysis element is a frameless chemical analysis film, a shift in the position of the element is more apt to occur and influence of the shift is more serious. Accordingly, the present invention is particularly useful when the chemical analysis element is a frameless chemical analysis film.

In accordance with one aspect of the present invention, there is provided a test element for use in a biochemical analysis apparatus in which sample liquid is spotted on a chemical analysis element taken out from a chemical analysis element cartridge, the chemical analysis element spotted with the sample liquid is held at a constant temperature and the optical density of the chemical analysis element is measured, thereby determining the concentration of a component to be analyzed in the sample liquid, the test element characterized by being substantially equal to the chemical analysis element in size and shape and having on at least one side thereof a density pattern for detecting the shift of the position of the test element from a predetermined position.

In accordance with another aspect of the present invention, there is provided a test element cartridge for dispensing a test element in a biochemical analysis apparatus in which sample liquid is spotted on a chemical analysis element, the chemical analysis element spotted with the sample liquid is held at a constant temperature and the optical density of the chemical analysis element is measured, thereby determining the concentration of a component to be analyzed in the sample liquid, the test element being substantially equal to the chemical analysis element in size and shape and having on at least one side thereof a density pattern for detecting shift of the position of the test element from a predetermined position, the cartridge characterized in that at least one said test element is stacked therein together with the chemical analysis elements.

In accordance with still another aspect of the present invention, there is provided a test element cartridge for dispensing a test element in a biochemical analysis apparatus in which sample liquid is spotted on a chemical analysis element taken out from a chemical analysis element cartridge in which a plurality of the chemical analysis elements are stacked, the chemical analysis element spotted with the sample liquid is held at a constant temperature and the optical density of the chemical analysis element is measured, thereby determining the concentration of a component to be analyzed in the sample liquid, the test element being substantially equal to the chemical analysis element in size and shape and having on at least one side thereof a density pattern for detecting shift of the position of the test element from a predetermined position, the cartridge characterized in that it is substantially equal to the chemical analysis element in size and shape and only the test elements are stacked therein.

Shift of the position of the test element from a predetermined position is optically detected. That is, a light beam is projected onto the test element and light transmitted through the test element or reflected by the test element is detected by a photodetector. The term "density pattern for detecting shift of the position of the test element from a predetermined position" means such a distribution of density that the output of the photodetector changes with the amount of shift of the center of the test element from the center of the light beam.

Since the test element is substantially equal to the chemical analysis element in size and shape, shift of the chemical analysis element from a predetermined position, for instance, on the take-out means or the transfer means can be estimated by running the biochemical analysis apparatus using the test element and measuring the transmitted light or the reflected light in one or more predetermined positions before effecting the normal biochemical analysis using the chemical analysis element.

For example, when a suction cup is employed as the take-out means or the transfer means, shift of the test element is caused by slip of the test element on the suction cup due to contaminant on the suction cup such as dirt and the like. Since the fact that the test element is shifted from the predetermined position indicates that the chemical analysis element will be shifted in the same manner. Accordingly, when a shift of the test element is detected, the shift of the chemical analysis element can be prevented by cleaning the suction cup.

The test elements may be stacked in a test element cartridge which is substantially the same as the chemical analysis element cartridge in size, shape and structure and may be taken out as required. Otherwise one or more test elements may be loaded in a chemical analysis element cartridge together with the chemical analysis element. This arrangement is advantageous in that a shift of the chemical analysis element due to a condition inherent to the particular cartridge can be estimated.

BRIEF DESCRIPTION OF THE DRAWINGS

FIG. 2 is a schematic perspective view showing a biochemical analysis apparatus to which the present invention is applied.

DESCRIPTION OF THE PREFERRED EMBODIMENT

Figure 1A:
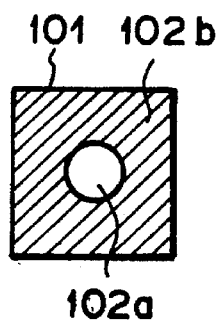
FIGS. 1A to 1F are schematic views respectively showing examples of the test pattern provided on the test element in accordance with the present invention.

In FIG. 2, a biochemical analysis apparatus 10 employing a test element in accordance with an embodiment of the present invention comprises a film supplier 11 in which a plurality of frameless chemical analysis films 1 are stored, an incubator 12 which is disposed beside the film supplier 11 and incubates the frameless chemical analysis films 1 at a constant temperature for a predetermined time, a film transfer means 13 which transfers the film 1 from the film supplier 11 to the incubator 12, a sample liquid supplier 14 in which a plurality of sample liquids such as serum, urine and the like are stored, a spotting means 15 which spots one of the sample liquids in the sample liquid supplier 14 onto the film 1 on the way to the incubator 12, and a light measuring system 16 disposed below the incubator 12.

Figure 3:
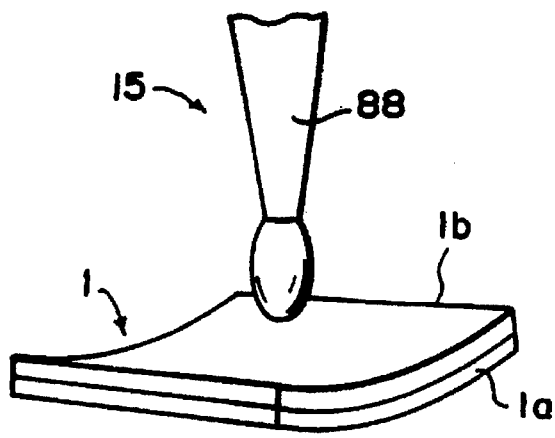
FIG. 3 is a perspective view showing a frameless chemical analysis film together with a spotting means.

As shown in FIG. 3, the frameless chemical analysis film 1 comprises a light-transmissive support sheet 1a formed of plastic film such as of polyethylene terephthalate and a reagent layer 1b including a spreading layer formed on the support sheet 1a. If desired, a protective layer formed of fibrous material resistant to rubbing such as cloth may be formed on the reagent layer and may double as the spreading layer.

In a dry state before use, the frameless chemical analysis film 1 is apt to curl or warp toward the reagent layer 1b and the degree of the curl varies depending on the kind of the reagent layer 1b, dryness and the like. The reagent layer 1b contains therein a reagent (chemical analysis reagent, immunoassay reagent or the like) which makes a coloring reaction when mixed with a predetermined component in the sample liquid and held at a constant temperature for a predetermined time (incubation). A plurality of kinds of frameless chemical analysis films 1 are prepared for respective analytes (a chemical component or a solid component to be analyzed in the sample liquid).

Figure 4:
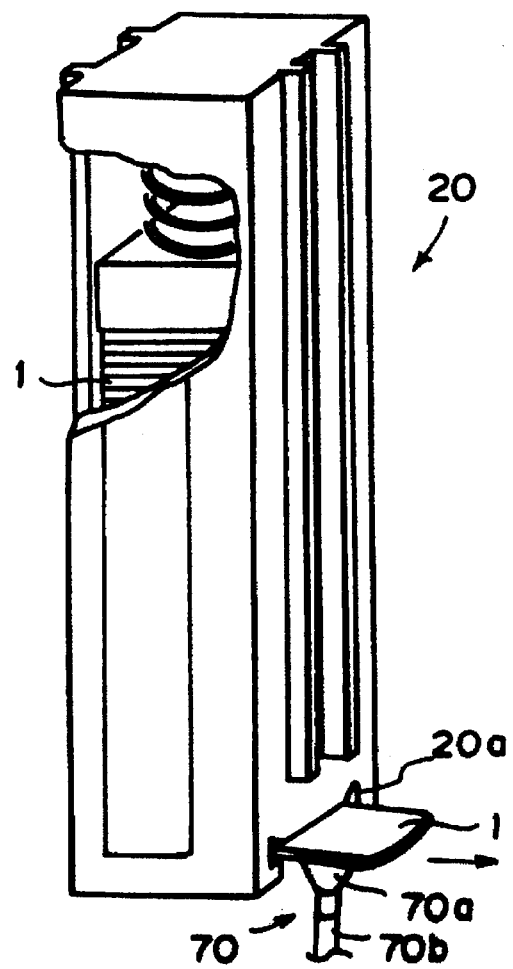
FIG. 4 is a perspective view showing a frameless chemical analysis film cartridge.

The frameless chemical analysis films 1 are stored in cartridges 20 shown in FIG. 4 for the respective analytes. In the cartridge 20, a plurality of frameless chemical analysis films 1 are stacked with the support sheet 1a facing downward. As shown in FIG. 2, the film supplier 11 is provided with a plurality of cartridge holding portions 22a which are arranged in inner and outer circles on a disk-like support 22 and a plurality of cartridges 20 loaded with the frameless chemical analysis films 1 are held in the respective cartridge holding portions 22a. The support 22 is supported for rotation on a base portion 24 and is rotated by a motor not shown so that a desired cartridge holding portion 22a is brought to a film take-out position where the film transfer means 13 takes out a frameless chemical analysis film 1 from the cartridge 20.

The support 22 is provided with a cover 25 which encloses the inner space of the film supplier 11. The cover 25 is provided with a pair of lidded openings 25a through which the cartridges 20 can be taken out and inserted into the cartridge holding portions 22a. A dehumidifying agent holding portion 27 is formed in the support 22 at the center thereof and dehumidifying agent (or desiccative agent) is loaded in the dehumidifying agent holding portion 27 through an lidded opening 25b formed in the cover 25. Thus, the inner space of the film supplier 11 is kept dry. A shutter (not shown) is provided in the lower surface of the cover 25 in the film take-out position. The shutter is opened when the film 1 is taken out and a suction pad 70 of the film transfer means 13 takes out the lowermost film 1 in the cartridge 20 through the shutter.

The incubator 12 comprises a disk-like body portion 40 which is supported to be rotated by a drive mechanism 41 disposed below the body portion 40 at the center thereof. A plurality of cells 42 are provided in the body portion 40 at predetermined intervals in the circumferential direction thereof. The frameless chemical analysis films 1 are incubated in the cells 42.

The film transfer means 13 for transferring the film 1 from the film supplier 11 to the incubator 12 comprises said suction pad 70 for taking out the film 1 from the cartridge 20, a horseshoe-like transfer member 73 which receives the film 1 on the suction pad 70 from below the film 1 with the reagent layer 1b facing upward and inserts the film 1 into the cell 42 in the incubator 12 through an opening which opens sideways, and a holding suction pad 76 which moves in and out the cell 42 from below the cell and holds the film 1 held by the transfer member 73 inside the cell 42.

As shown in FIG. 4, the take-out suction pad 70 comprises a suction cup 70a which is directed upward and attracts the lower side of the support sheet 1a of the film 1. The suction cup 70a is supported on a base portion 70b which is moved back and forth and up and down by a drive mechanism (not shown) and is connected to a suction pump (not shown) through a vacuum tube.

The take-out suction pad 70 is moved upward into the cartridge 20 through an opening formed in the bottom of the cartridge 20 and is brought into contact with the support sheet 1a of the lowermost film 1. Then the suction pad 70 holds the lowermost film 1 under a suction force and is slightly moved downward, whereby the film 1 is reshaped into a predetermined warped-shape. In this state, the suction pad 70 is moved laterally to take out the film 1 through an opening 20a in a side wall of the cartridge 20. Then the suction pad 70 is moved downward outside the film supplier 11 through the opening in the cover 25. After thus taking out the film 1, the suction pad 70 transfers the film 1 to a spotting position where the sample liquid is spotted onto the film 1.

Figure 5:
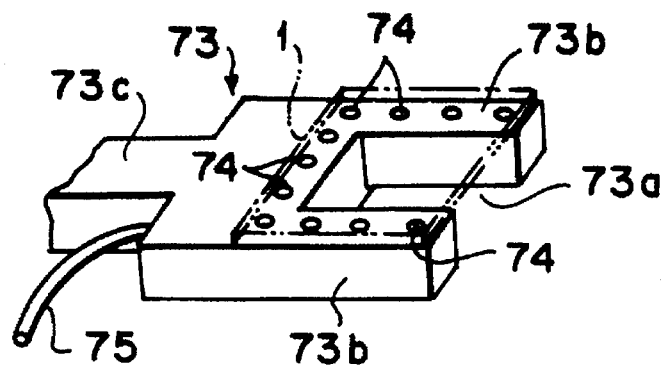
FIG. 5 is a perspective view of a major part of the transfer member.

As shown in FIG. 5, the transfer member 73 is like a horseshoe in shape and has a flat upper surface. That is, the transfer member 73 is bifurcated in the front end portion to form a pair of arm portions 73b extending on opposite sides of a cutaway portion 73a, and a plurality of suction holes 74 are formed to surround the cutaway portion 73a and to open in the upper surface of the transfer member 73. The suction holes 74 are connected to a suction pump (not shown) through a vacuum tube 75. The base portion 73c of the transfer member 73 is connected to a drive mechanism (not shown) to be inserted into the cell 42 in the incubator 12 through the side opening of the incubator 12.

Figure 6A:
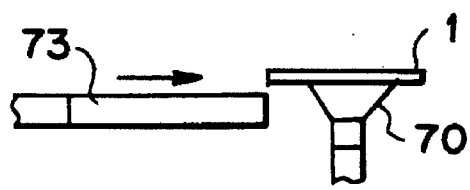
FIGS. 6A to 6C are schematic views for illustrating the procedure of transferring the frameless chemical analysis film from the suction pad to the transfer member.
Figure 6B:
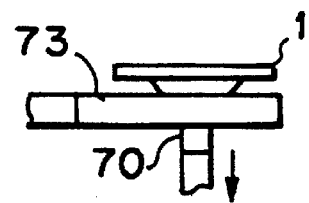
Figure 6C:
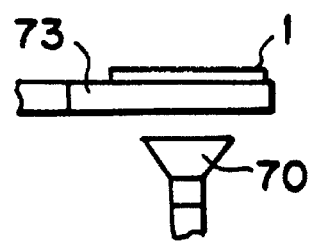

When the transfer member 73 receives the film 1 from the suction pad 70, the transfer member 73 is moved toward the suction pad 70 holding the film 1 as shown in FIG. 6A and is stopped in a position where the suction pad 70 is in the cutaway portion 73a of the transfer member 73 with the film 1 positioned above the cutaway portion 73a as shown in FIG. 6B. Then the suction pad 70 is moved downward below the transfer member 73 leaving the film 1 on the transfer member 73 as shown in FIG. 6C. The film 1 left on the transfer member 73 is held thereon under the suction force provided through the suction holes 74. When the position of the suction pad 70 relative to the film 1 held thereby the is accurately controlled, the position of the transfer member 73 relative to the film 1 can be accurately controlled and a predetermined amount of the sample liquid can be accurately spotted onto the center of the reagent layer 1b of the film 1 held by the transfer member 73.

The sample liquid supplier 14 comprises a turntable 85 which is rotated by a drive mechanism 86. The turntable 85 holds a plurality of sample tubes 87 filled with sample liquids which are arranged along the circumferential edge of the turntable 85 and is rotated to bring the sample tubes 87 to a sample liquid supplying position one by one. A plurality of nozzle tips 88 which are mounted on a spotting nozzle 91 to be described later are held on the turntable 85 inside the sample tubes 87.

The spotting means 15 for spotting the sample liquid onto the film 1 comprises the spotting nozzle 91 which sucks and discharges the sample liquid, and a nozzle tip 88 like a pipette is demountably mounted on the nozzle 91. The nozzle 91 is moved up and down and rotated by a drive mechanism 92. That is, the nozzle 91 sucks the sample liquid from the sample liquid supplier 14, is moved to the film 1 held by the transfer member 73, and then spots the sample liquid onto the film 1. The nozzle tip 88 is changed every time the sample liquid is changed.

For example, when the film attracting surface of the take-out suction pad 70, the transfer member 73 or the holding suction pad 76 forming the film transfer means 13 are contaminated, the film attracting force is weakened and the film 1 is easily shifted from the regular position on the suction means with a weak external force. Such an accident, can be avoided by use of a test element 101 which has a two-dimensional density pattern (will be referred to as "test pattern", hereinbelow) such as shown in FIGS. 1A to 1F. The test element 101 is the same as the frameless chemical analysis film 1 in size and shape.

Figure 7:
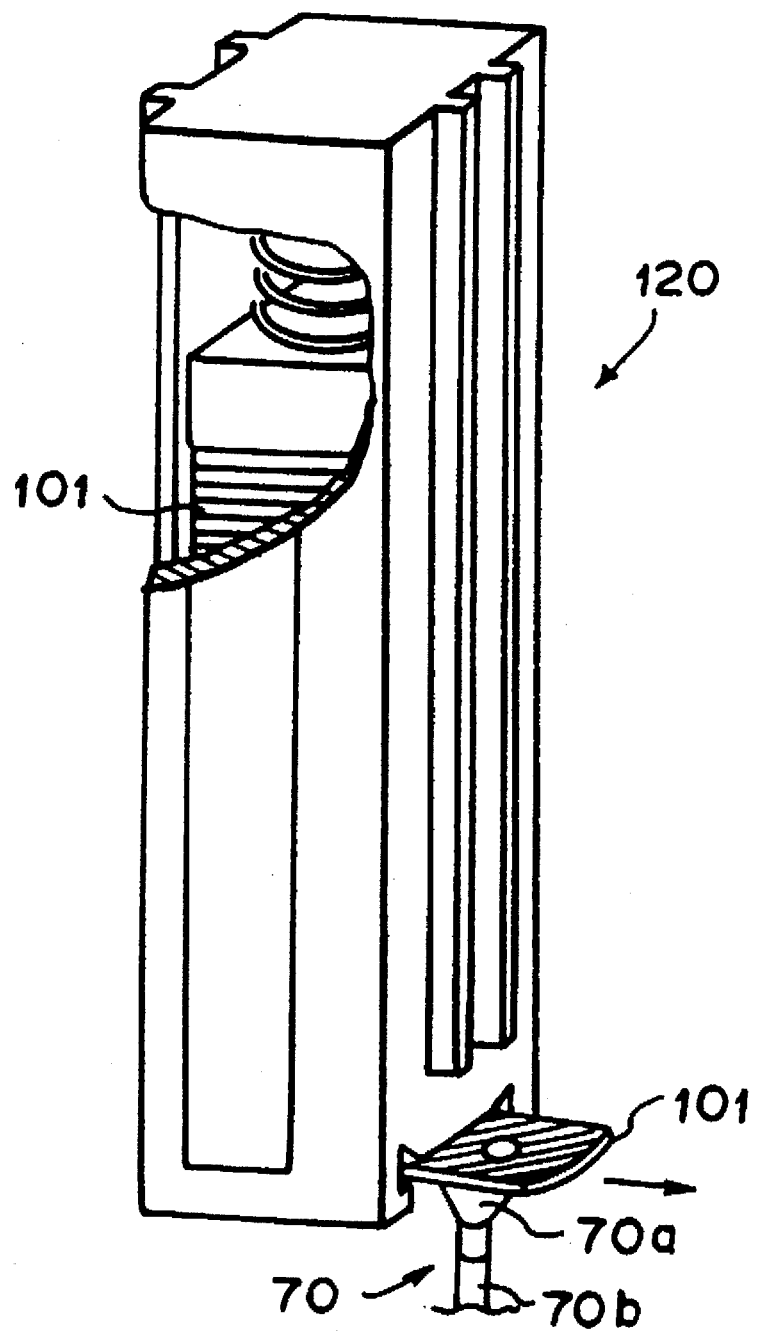
FIG. 7 is a perspective view showing the manner of taking out the test element from the test element cartridge.
Figure 8:
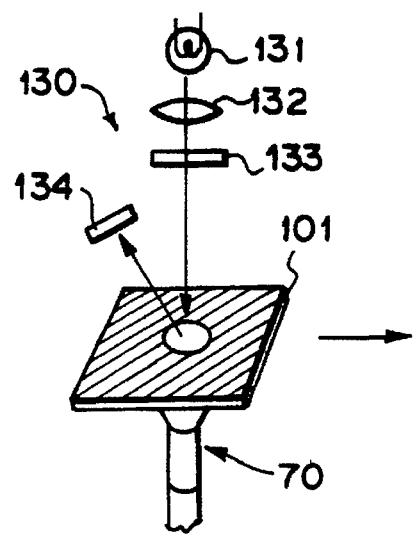
FIG. 8 is a schematic perspective view showing the light measuring test section.

The test elements 101 are stacked in a test element cartridge 120 shown in FIG. 7 and are taken out from the cartridge 120 by the take-out suction pad 70 to be subjected to a shift test in a light measuring test section 130 shown in FIG. 8. As will be described in more detail later, in the test section 130, a light beam is projected onto the test element 101 while transferring the test element 101, and light reflected by the test element 101 is detected by a photodetector, and whether the test element 101 is in the regular position is determined on the basis of the output of the photodetector.

As the test pattern, various density patterns (or color developing patterns) can be employed so long as the following conditions (1), (2) and (3) are satisfied.

Figure 9A:
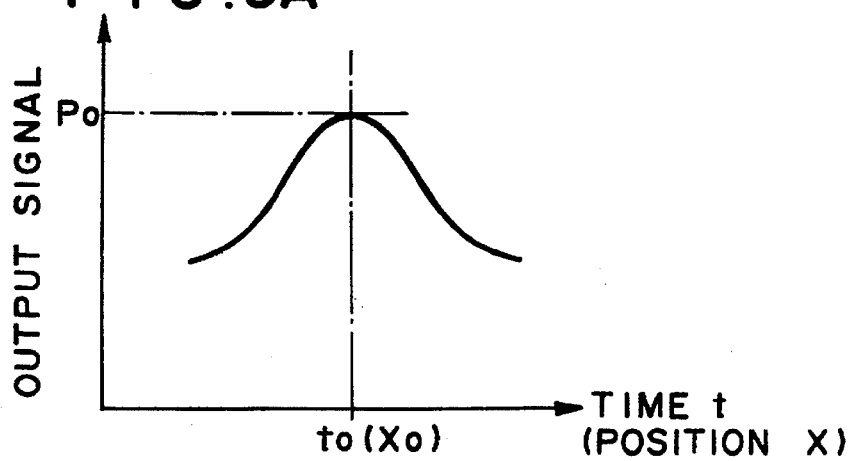
FIGS. 9A and 9B are graphs showing examples of the signal pattern output from the photodiode.
Figure 9B:
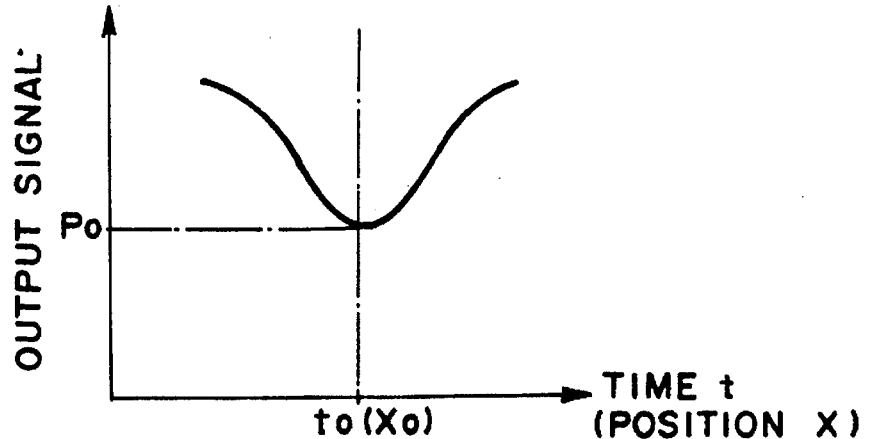

(1) A test pattern having a density distribution which provides a symmetric photodetector output distribution as shown in FIG. 9A or 9B when the test element 101 is held in the regular position.

(2) A test pattern having a density distribution which maximizes or minimizes the photodetector output when the center of the test pattern coincides with the center of light measurement.

(3) A test pattern having a density distribution which provides a change in the photodetector output at least about 10% of the dynamic range of light measurement.

Figure 1B:
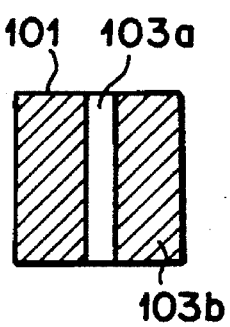
Figure 1C:
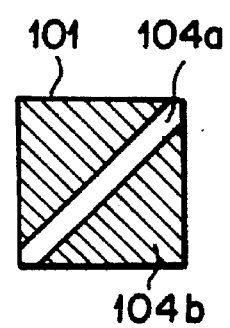
Figure 1D:
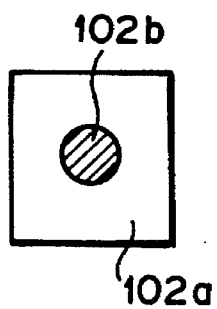
Figure 1E:
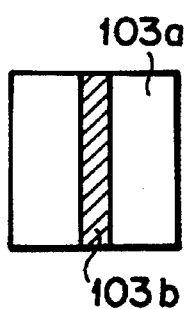
Figure 1F:
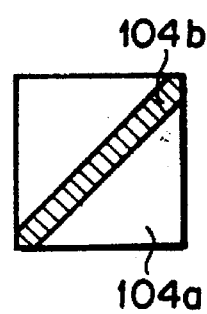

For example, the test patterns shown in FIGS. 1A to 1F can be employed. The test pattern shown in FIG. 1A has a circular low density portion 102a at the center and a high density portion 102b around the low density portion 102a. The test pattern shown in FIG. 1D is the reverse of that shown in FIG. 1A and has a circular high density portion 102b at the center and a low density portion 102a around the low density portion 102a. The test pattern shown in FIG. 1B has an elongated low density portion 103a which vertically extends at the center and has a uniform width and high density portions 103b on opposite sides of the low density portion 103a. The test pattern shown in FIG. 1E is the reverse of that shown in FIG. 1B and has an elongated high density portion 103b which vertically extends at the center and has a uniform width and low density portions 103a on opposite sides of the high density portion 103b. The test pattern shown in FIG. 1C has an elongated low density portion 104a which diagonally extends and has a uniform width and high density portions 104b on opposite sides of the low density portion 103a. The test pattern shown in FIG. 1F is the reverse of that shown in FIG. 1C and has an elongated high density portion 104b which diagonally extends and has a uniform width and low density portions 104a on opposite sides of the low density portion 104b.

The test element 101 is the same as the frameless chemical analysis film 1 in size, shape and weight, and comprises the support sheet 1a and the reagent layer (protective layer) 1b which are the same as those in the frameless chemical analysis film 1 with emulsion for producing the test pattern sandwiched between the layers 1a and 1b. Further, the test element cartridge 120 is the same as the frameless chemical analysis film cartridge 20 except that it is loaded with the test elements 101 instead of the frameless chemical analysis films 1. Accordingly, when the test element 101 taken out from the test element cartridge 120 is held in the regular position, it can be expected that the frameless chemical analysis film 1 can be taken out and transferred in the regular position.

The test element cartridge 120 is loaded in one or more of the cartridge holding portions 22a in the film supplier 11.

As shown in FIG. 8, the test section means 130 comprises a light source 131, a focusing lens 132, a filter 133 and a photodiode 134. A light beam emitted from the light source 131 is projected onto the test element 101 through the focusing lens 132 and the filter 133 and the photodiode 134 receives reflected light from the test element 101.

The test element 101 held by the take-out suction pad 70 is transferred so that its center passes through the center of the light beam focused by the focusing lens 132 (the center of light measurement) if the test element 101 is held in the regular position on the suction pad 70 and measurement of light is initiated when the suction pad 70 passes a predetermined position.

The light source 131 emits a predetermined amount of light, and accordingly the amount of reflected light received by the photodiode 134 is determined by the position of the test pattern in which the light is reflected.

That is, when the test element 101 is held in the regular position on the suction pad 70, the center of the test element 101 coincides with the center of the light beam at time $t_0$ (FIGS. 9A and 9B), when the output of the photodiode 134 is maximized as shown in FIG. 9A in the case of the test patterns shown in FIGS. 1A to 1C or minimized as shown in FIG. 9B in the case of the test patterns shown in FIGS. 1D to 1F. On the other hand, when the test element 101 is held in a position shifted from the regular position on the suction pad 70, the pattern of the signal from the photodiode 134 shifts in the direction of the abscissa from that shown in FIG. 9A or 9B or becomes different in shape from that shown in FIG. 9A or 9B.

Figure 10A:
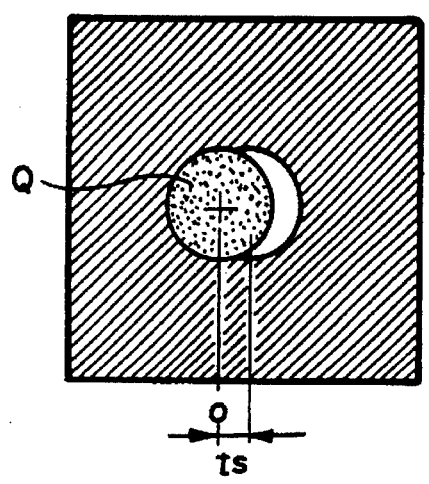
FIGS. 10A and 10B are views for illustrating the condition where the position of the test element is shifted in the direction of transfer of the element relative to the suction pad and the signal pattern obtained in such a case.
Figure 10B:
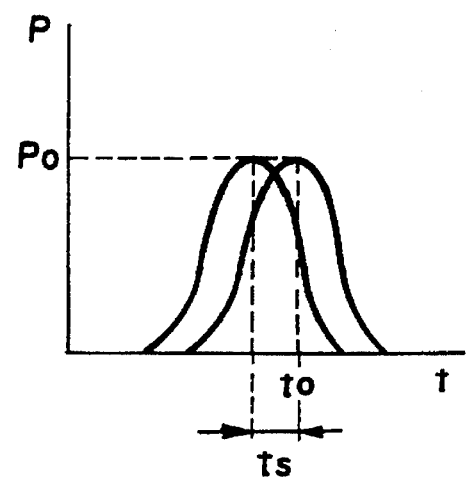
Figure 11A:
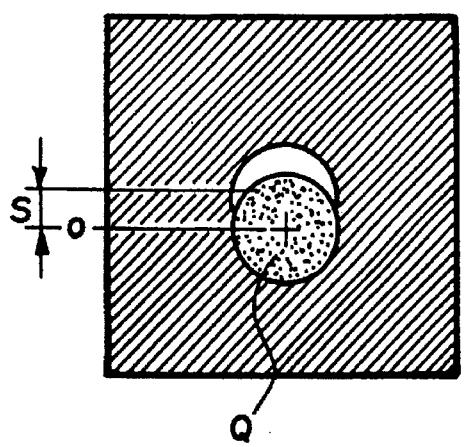
FIGS. 11A and 11B are views for illustrating the condition where the position of the test element is shifted perpendicularly to the direction of transfer of the element relative to the suction pad and the signal pattern obtained in such a case.
Figure 11B:
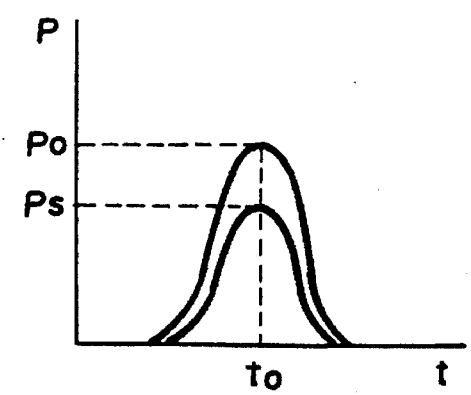

For example, when the test pattern on the test element 101 is as shown in FIG. 1A and the position of the test element 101 is shifted from the regular position on the suction pad 70 by a distance corresponding to a time interval $t_s$ in the direction of transfer of the test element 101 (in the direction of the arrow in FIG. 8), the center of the test pattern is away from the center of the light beam (indicated at Q) by a distance corresponding to a time interval $t_s$ at the time $t_0$ as shown in FIG. 10A and the pattern of the signal from the photodiode 134 shifts in the direction of the abscissa from that shown in FIG. 9A by the distance corresponding to the time interval $t_s$ as shown in FIG. 10B. Further, when the position of the test element 101 is shifted from the regular position on the suction pad 70 by a distance S perpendicularly to the direction of transfer of the test element 101, the center of the test pattern or the low density portion does not fully coincide with the light beam Q as shown in FIG. 11A and the peak value of the signal pattern is lowered to Ps, which is lower than that $P_0$ when the test element 101 is in the regular position, as shown in FIG. 11B.

Thus, by calculating the shift from the time $t_0$ of the time at which the signal for the test element 101 was maximized (or the distance between the position of the peak of the signal pattern for the test element 101 and the position $X_0$ of the peak of the regular signal pattern) or the difference in the peak values $P_0$ and Ps, the amount of shift of the test element 101 from the regular position and the direction of the shift can be detected on the basis of the relation between the amount of light and the amount of shift which is calculated in advance.

Since the element is generally transferred in the direction perpendicular to one of pairs of opposed sides and parallel to the other pair of opposed sides, when the test pattern shown in FIG. 1B or 1E is employed in place of that shown in FIG. 1A or 1D, the accuracy in measurement of the shift of the test element 101 in one direction can be improved. When the test pattern shown in FIG. 1C or 1F is employed in place of that shown in FIG. 1A or 1D, the accuracy in measurement of the shift of the test element 101 in two directions perpendicular to each other can be improved.

The test section 130 is disposed between the film take-out position and the spotting position.

Though, in the description above, detection of shift of the position of the test element 101 on the take-out suction pad 70 is described, shift of the test element 101 on the transfer member 73 or the holding suction pad 76 can also be detected in the similar manner. In this case, a light measuring test section similar to the test section 130 described above is disposed near the path of the transfer member 73 or the suction pad 76.

Further shift of the test element 101 in the cell 42 in the incubator 12 can also be detected by employing a light measuring system 16 having a function similar to that of the light measuring test section means 130 described above.

Though, in the embodiment described above, the test elements 101 are loaded in the test element cartridge 120 exclusively for the test elements and the test element is taken out from the test element cartridge 120 as needed, one or more test elements may be inserted into the stack of the frameless chemical analysis films in a frameless chemical analysis film cartridge 20.

Further, the test element may be arranged so that the test pattern is detected through transmitted light instead of reflected light.

Though, in the embodiment described above, the test element 101 is not provided with any frame since the frameless chemical analysis film is employed as the chemical analysis element, a test element with frame is used when aforesaid chemical analysis slide is employed as the chemical analysis element.

If necessary whether the light measuring opening through which the light measuring system 16 measures the optical density of the frameless chemical analysis film 1 is precisely positioned in a predetermined position may be detected in the similar manner by providing a test pattern on the surface of a cap which is fitted in the light measuring opening.

It is preferred that the spring for urging downward the stack of the test elements 101 in the test element cartridge 120 be, for instance, twice as strong as the spring for urging downward the stack of the frameless chemical analysis films 1 in the frameless chemical analysis film cartridge 20 so that the accuracy of the detection is further improved. That is, when the test element 101 under such a condition can be smoothly taken out from the cartridge 120 without shift of the test element 101, the attracting force of the suction pad 70 may be considered satisfactory, which ensures that the frameless chemical analysis film 1 pressed under a lighter force should be able to be taken out more smoothly without fear of shift in position on the suction pad 70.

Further it is possible to load test elements slightly larger or smaller than the frameless chemical analysis film 1 and to determine whether the attracting force of the suction pad 70 is satisfactory by detecting whether such different size test elements can be smoothly taken out from the cartridge 120 without a shift of the test elements.

What is claimed is:

1. A test element for use in detecting a positional shift of a chemical analysis element during transfer thereof in a biochemical analysis apparatus, said biochemical analysis apparatus including a supplier for storing and supplying a plurality of chemical analysis elements and at least one test element; an incubator for incubating the chemical analysis elements; a transfer means for transferring the chemical analysis elements one-by-one from the supplier to the incubator; a sample liquid supplier for storing a plurality of sample liquids; a spotting means for spotting a selected one of the sample liquids onto a selected one of the chemical analysis elements before entering the incubator; means for determining the concentration of a component of the selected sample liquid in the selected chemical analysis element after incubation; and a test section means for detecting a positional shift of said test element from a predetermined position during transfer by said transfer means, wherein said test element is substantially equal in size and shape with respect to said chemical analysis element and includes on at least one side thereof a density pattern which is operative for detection by said test section means, thereby to detect a positional shift of said test element from the predetermined position which in turn is indicative of a corresponding positional shift of said chemical analysis element during transfer.

2. The combination according to claim 1, wherein each of said chemical analysis elements is a frameless chemical analysis film.

3. The combination according to claim 1, wherein said test section means is disposed between said supplier and said spotting means.

4. The combination according to claim 1, wherein said test section means comprises a light source and a photodiode such that a light beam from said light source is projected onto said at least one test element, and said photodiode receives reflected light from said at least one test element in an amount based on a position of said density pattern.

5. The combination according to claim 1, further comprising a cartridge disposed in said supplier and for housing said at least one test element.

6. The combination according to claim 5, wherein said at least one test element is stacked together with the plurality of chemical analysis elements in said cartridge.

* * * * *